US00PP12171P2

(12) United States Plant Patent
Turner, Sr.

(10) Patent No.: US PP12,171 P2
(45) Date of Patent: Oct. 30, 2001

(54) *NERIUM OLEANDER* PLANT-'TURNER'S 6-667'

(76) Inventor: Ted Leon Turner, Sr., 6503 S. Padre Island Dr., Corpus Christi, TX (US) 78412

( * ) Notice: Subject to any disclaimer, the term of this patent is extended or adjusted under 35 U.S.C. 154(b) by 0 days.

(21) Appl. No.: 09/428,439

(22) Filed: Oct. 28, 1999

(51) Int. Cl.[7] ..... A01H 5/00
(52) U.S. Cl. ..... Plt./233
(58) Field of Search ..... Plt./233

(56) References Cited

U.S. PATENT DOCUMENTS

P.P. 5,378 12/1984 Turner, Sr. .

*Primary Examiner*—Bruce R. Campell
*Assistant Examiner*—June Hwu
(74) *Attorney, Agent, or Firm*—Stewart N. Rice

(57) ABSTRACT

A *Nerium oleander* plant which has a petite and upright habit of growth, being particularly characterized by long blooming periods and the unique color of its inflorescnce and its habit of growth, the flowers being a white color with areas of pale yellow in the corona or throat, and which flowers grow in tight cymes or clusters resembling pompons.

1 Drawing Sheet

DESCRIPTION OF THE INVENTION

The present invention relates to a new and distinct variety, of petite size, of *Nerium oleander* which was originated by me as a seedling by selection and crossing. I crossed a *Nerium oleander* 'Petite Salmon' (non-patented) with a *Nerium oleander* 'Turner's Shari D'. The 'Petite Salmon' is a petite size plant which produces single flowers which are bright salmon pink in color. The 'Petite Salmon' is a common and commercially available variety which was originated at the Los Angeles Arboretum in 1973. 'Turner's Shari D' is the subject of U.S. Plant Pat. No. 5,378 issued Dec. 25, 1984, to Ted L. Turner, Sr., and this plant is an intermediate to full size plant with flowers which are soft buff yellow with tinges of pink. However, in making my crosses, I observed that pollination could have been accomplished by bees from unknown plants. Thus unknown parentage could have been introduced by the bees even though I did not purposely introduce any parentage other than the 'Shari D' and the 'Petite Salmon'.

From the group of seedlings I observed a plant, being the plant claimed herein, having a new and distinct color of flowers, and from cuttings of such plant I was able to asexually reproduce plants having the same characteristics and flower color as the original seedling. The plant observed for this patent application had been grown in a greenhouse, was in a five gallon container, and was about four years old. All of the descendant plants showed the same characteristics as the original seedling, and as a result of extensive observations and tests which are not described in full herein for sake of brevity, it is my opinion and I am convinced that my new plant is a new variety of *Nerium oleander* which is distinguished from all other varieties of which I am aware as evidenced by the following unique combination of principal characteristics which are outstanding therein:

(1) An upright habit of growth and of petite size making it especially suitable for hedges and as a pot plant, or to add garden color;

(2) An ability to be asexually reproduced;

(3) An ability to flower substantially throughout the year with long continuous blooming periods;

(4) The ability to bloom in partial shade, such as morning sun only;

(5) The ability to be a good greenhouse bloomer and bloom year around in a greenhouse;

(6) The ability to initially grow and flower in relatively small pots as small as about eight centimeters in diameter although, the plant should be placed in a larger pot of at least 30 centimeters to obtain larger growth;

(7) The ability to produce a flower having a white color with areas of yellow in the corona;

(8) The ability to produce a plant having flowers arranged in tight cymes or clusters resembling pompons; and (9) The ability to grow in windy conditions.

Asexual reproductions of my new variety as by cuttings shown that the foregoing characteristics and distinctions come true to form and are established and transmitted through succeeding propagations. The ongoing planned breeding program which resulted in the plant described herein and the initial asexual reproduction of this plant have taken place in a nursery in Corpus Christi, Nueces County, Tex.

The accompanying FIGURE is a photograph of a typical flower on the plant of my new variety more clearly illustrating the colors present on each flower. The true color of the foliage and flowers is described in the following description and is depicted in the FIGURE which depicts the color as nearly as true as is reasonably possible in a color illustration of this type.

The following is a detailed description of my new variety of *Nerium orleander*, which color numbers are in accordance with the Pantone Matching System of colors for printing inks, Pantone Color Formula Guide 747 XR, 1987–1988, published by Pantone, Inc. Terms used to describe colors are those of ordinary significance.

The Plant

Growth habit: Upright, petite size; the height of an unpruned mature plant will be from about 1.5 to 2.5 meters, but has not yet been determined; fast growing in shady areas and slower in full sun. The plant grows full from just about ground level upward, with the width of the plant about 40% to 75% of the height. The plant is slightly smaller than the *Nerium oleander* 'Petite Salmon' referenced above, and much smaller than the *Nerium oleander* 'Shari D' referenced above.

Hardiness: Adapted to seaside planting as it tolerates soil with relatively high salt content; tolerates droughts; will not withstand prolonged and severe freezing weather; most suitable for the Southern United States from California to Florida, in the areas known as Zones 9 and 10; withstands heat and light and grows either in full sun or in partial shade (up to 50% shade) such a morning sun only; can be started and will bloom in small pots as small as about eight centimeters in diameter, although the plant should be transferred to a larger pot of 30 centimeters or larger to obtain a larger growth.

Branches: The plant is relatively tightly branched from just above ground level with main branches and branchlets ascending. The plant does not develop a central leader or trunk. New growth of branches is a light to medium green, Color No. 390U, changing to light greenish brown in color, Color No. 4505U, as branches mature. The old or matured wood is a pale brownish gray, Color No. 4U.

Blooming period: Under outside conditions, blooms off and on substantially the entire year, being in bloom about 75% of the time. The plant will bloom substantially all the time in a greenhouse.

The Foliage

Type: Broadleaf evergreen; numerous; petioled; grow in a whorl with three leaves in each whorl.

Shape: Linear-lanceolate, with entire margins. Apex is more or less acuminate and slightly non-symmetrical, and base is acute.

Petioles: Length, from about 3 to 5 mm; color pale green, Color No. 397U.

Leaf size: Length of mature leaf from about 100 to 160 mm; width of mature leaf about 15 to 22 mm. Size of leaf varies according to sunshine conditions at the time the leaf is produced, with larger leaves being produced under cloudy conditions than unde sunny conditions.

Venation: Midrib on under surface prominent and readily apparent and is pale green, Color No. 586U; on upper surface midrib is clearly visible and slightly recessed, and is pale green, Color No. 584U; lateral veins are not readily apparent on upper surface but under surface contains numerous, delicate, almost parallel lateral veins which are readily apparent, the lateral veins being substantially perpendicular to the midrib.

Leaf color — Mature leaves: upper surface — dark green, Color No. 575C; under surface lighter in color than upper surface, being a medium green, Color No. 5757U.

New leaves: Slightly lighter and brighter in color than mature leaves, upper surface — dark green, Color No. 576C, the under surface being a medium green, Color No. 583U.

Leaf texture: Tough, leathery; smooth.

*Upper surface.*—Non-glossy.

*Lower surface.*—Dull.

The Inflorescence

Position and abundance: Flowers cluster at twig or branch ends in terminal cymes, with cymes appearing at various positions from the lower part to the upper part of the plant. Each cyme is tightly clustered with generally about 8 to 12 flowers each, although some cymes may contain up to about 20 flowers each. Each cyme resembles a pompon because of the tightness of the cluster of flowers.

Form: Single, regular; pediceled; petals united in a sympetalous corolla; salverform; tube spreads into five limbs or lobes; each flower is about 35 to 40 mm across; corona conspicuous at junction of tube and spreading limb, corona about 8 to 10 mm in diameter and a depth of about 15 mm which is much shorter than spreading limbs, the corona having five crownlike appendages, each appendage corresponding to a limb, most appendages being 4 to 6 toothed at their outer ends.

Buds: Limbs convolute in the bud, obliquely apiculate, the folds twisting counterclockwise when viewing down onto the tip of the bud, such the limbs of the flower twist slightly clockwise when viewing down into the flower.

Calyx: Of 5 persistent sepals, imbricate in the bud, lanceolate, acuminate, about 6 to 9 mm long. The sepals have a relatively smooth surface texture.

Stamen: 5 stamens; filaments partly adnate to corolla tube; anthers with 2 basal tails, apex long-attenuate, hairy. The stamens are about 10 to 12 mm in length, with a medium yellow color, Color No. 121C.

Pistil: The syle portion of the pistil is white in color with the outer end or stigma portion being a pale yellow color, and with the pistil being approximately 10 mm in length.

Color of flower: Limbs or petals of the corolla in new flowers are bright white color. There is no corresponding white color in the Pantone Matching System, although the color of the petals are similar to the opaque white ink used in the Pantone Matching System of Colors for printing ink. As is the case with most oleanders, blooms produced under a full sun may be lighter in shade than those produced on cloudy days. The corona is pale yellow, being a pale version of Color No. 127U. The outside of the corolla tube of each flower is golden yellow, Color No. 120U. The calyx and sepals are light green, Color No. 372U.

Fragrance: The flowers have no appreciable fragrance.

Color of buds: Light yellow, Color No. 393U.

To further describe my new variety of *Nerium oleander*, it is very similar in height to the other well-known petite size *Nerium oleanders* which grow in an upright manner, except for the color of the flowers, and except that my new variety appears to be slightly more upright and the flowers grow in fairly tight clusters similar to pompons. I am not aware of any *Nerium oleander* of a petite size having a flower and growth habit which is the same as that produced by my plant.

VARIETY NAME

The proposed variety name of my new plant is *Nerium oleander* 'Turner's 6-667'.

I claim:

1. A new and distinct variety of petite size *Nerium oleander* plant substantially as shown and described, having an upright habit of growth making it especially suitable for hedges, having an ability to be asexually reproduced, having the ability to flower off and on throughout the entire year with long continuous blooming periods, having the ability to grow in full sun or in partial shade, being an excellent greenhouse plant, and being particularly characterized by its petite size combined with the unique color of its inflorescence and its growth habit, and having terminal cymes of flowers which are tightly clustered, the flowers being a white color with throats or coronas of a pale yellow.

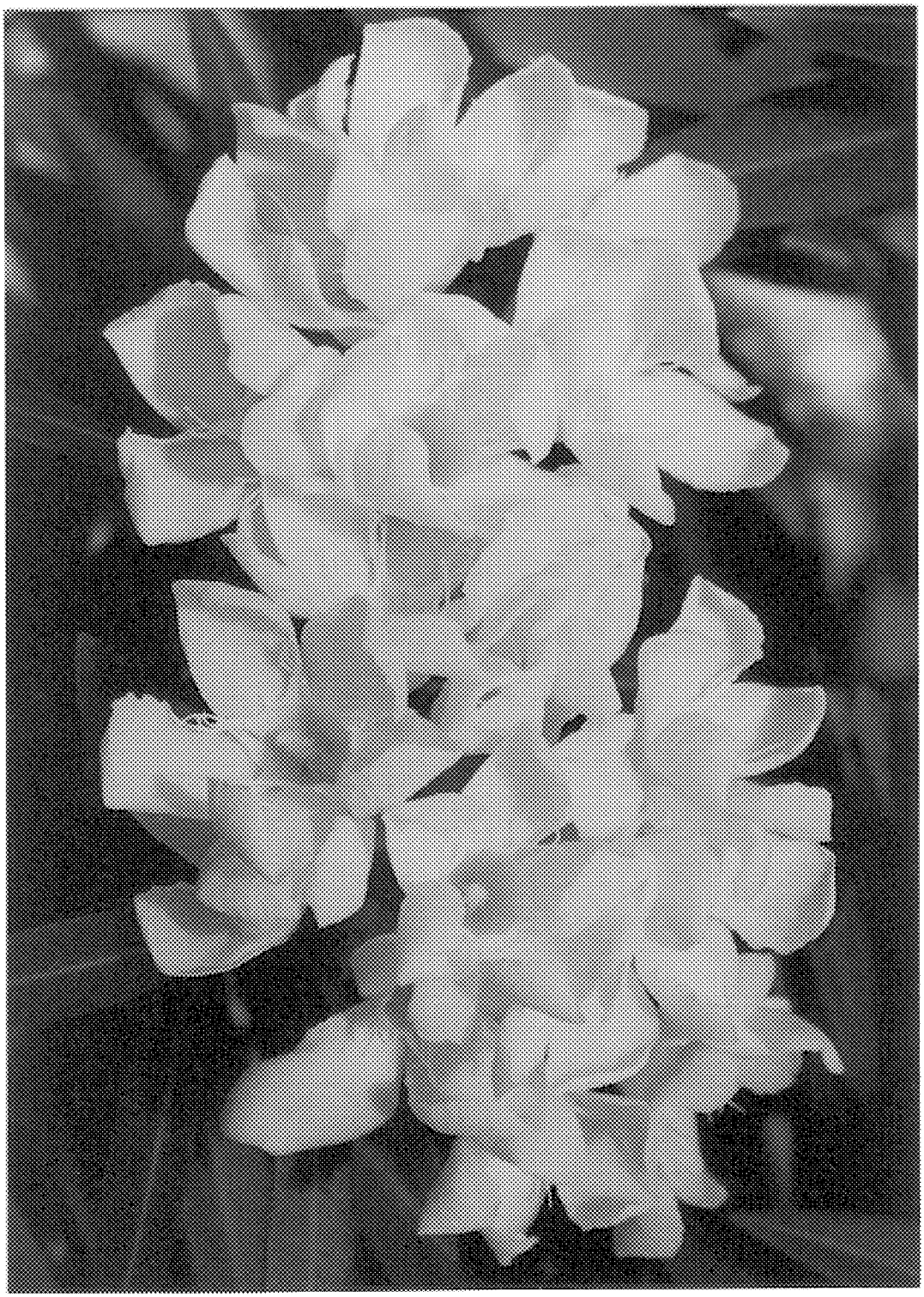

* * * * *